(12) United States Patent
Austin et al.

(10) Patent No.: US 6,468,527 B2
(45) Date of Patent: Oct. 22, 2002

(54) BIOLOGICAL BIOADHESIVE COMPOSITION AND METHODS OF PREPARATION AND USE

(76) Inventors: Sam L. Austin, 1902 S. 10th Ave., Boise, ID (US) 83605; Thomas E. Davis, 1902 S. 10th Ave., Boise, ID (US) 83605

( * ) Notice: Subject to any disclaimer, the term of this patent is extended or adjusted under 35 U.S.C. 154(b) by 0 days.

(21) Appl. No.: 09/888,310

(22) Filed: Jun. 22, 2001

(65) Prior Publication Data

US 2002/0018804 A1 Feb. 14, 2002

Related U.S. Application Data

(60) Provisional application No. 60/213,806, filed on Jun. 22, 2000.

(51) Int. Cl.[7] ............................................... A61K 38/48
(52) U.S. Cl. ........................ 424/94.64; 424/94.1; 514/2; 514/169
(58) Field of Search ............................. 514/2, 167–182; 424/94.64, 94.1

(56) References Cited

U.S. PATENT DOCUMENTS 5,962,420 A    10/1999    Edwardson et al. ........... 514/21

FOREIGN PATENT DOCUMENTS

| DE | 3037270      | 5/1982 | ........... A61L/15/04 |
| EP | 0 068 149    | 5/1982 | ........... A61L/15/04 |
| WO | WO 81/00516  | 5/1981 | ............ A61K/9/18 |
| WO | WO 94/20133  | 9/1994 | ......... A61K/37/547 |
| WO | WO 96/17633  | 3/1996 | ........... A61L/25/00 |

*Primary Examiner*—Jose' G. Dees
*Assistant Examiner*—Konata M George
(74) *Attorney, Agent, or Firm*—Pedersen & Co., PLLC; Ken J. Pedersen; Barbara S. Pedersen

(57) ABSTRACT

The present invention relates generally to the preparation and use of novel enhanced biological tissue adhesives which rely on combining fibrinogen and thrombin. More particularly, the present invention relates to a method of preparing a fibrin sealant whereby said sealant is formed by reconstituting the fibrinogen component in the presence of various critical biological and non-biological agents. The invention further relates to a novel method of using said enhanced fibrin sealant whereby the sealant and accompanying agent are delivered directly to a critical site within the body and sealed in place due to the bio-static quality of the sealant resulting in enhanced therapeutic value derived by the prolonged presence, and optionally time-released delivery, of said accompanying agent at the critical site.

14 Claims, 1 Drawing Sheet

BIOLOGICAL BIOADHESIVE COMPOSITION AND METHODS OF PREPARATION AND USE

This application claims priority from,. U.S. Provisional Patent Application Ser. No. 60/213,806, filed on Jun. 22, 2000, entitled "Biological Bioadhesive Composition and Methods of Preparation and Use" the disclosure of which is incorporated herein by this reference.

BACKGROUND OF THE INVENTION

1. Field of the Invention

The present invention relates generally to the preparation and use of novel enhanced biological tissue adhesives which rely on combining fibrinogen and thrombin. More particularly, the present invention relates to a method of preparing a fibrin sealant whereby said sealant is formed by reconstituting the fibrinogen component in the presence of various critical biological and non-biological agents. The invention further relates to a novel method of using said enhanced fibrin sealant whereby the sealant and accompanying agent are delivered directly to a critical site within the body and sealed in place due to the bio-static quality of the novel sealant resulting in enhanced therapeutic value derived, for example, by the prolonged presence of said accompanying agent at the critical site. The bio-static quality of the novel composition makes it possible to deliver a particular therapeutic agent to a specific critical site within the body and provide for a sustained, time-released delivery of said agent at said critical site.

2. Related Art

Fibrin sealants are well known and used extensively in various clinical settings. Said sealants are indicated as adjuncts to hemostasis in surgeries when control of bleeding by conventional surgical techniques, including suture, ligature, and cautery is ineffective or impractical. For instance, fibrin sealants have been shown to be effective in patients undergoing reoperative cardiac surgery (J. Rousou, et al., Journal of Thoracic and Cardiovascular Surgery, vol.97, no.2, pp 194–203, February 1989), spinal neurosurgery (P. Knoringer, *Fibrin Sealing in Spinal Neurosurgery*, 1986), general cardiac surgery (P. M. McCarthy, et al., *Fibrin Sealant: The Cleveland Clinic Experience*, 1991), pulmonary surgery, (M. Dahan et al., *The Importance of Biological Glue for the Prevention of Air Leakage in Pulmonary Surgery*, Materials and Methods, pp 113–116, 1991), liver and spleen surgery (H.W. Waclawiczek, *Fibrin Sealing in Liver and Spleen Surgery*, 1994), and neurosurgical procedures (C. Shaffrey, et al., Neurosurgery, vol.26, No.2, pp 207–210, 1990).

Use of fibrin glue and methods for its preparation and use are described by Hirsh et al. U.S. Pat. No. 5,643,192. Hirsh, however, does not envision the reconstitution of the fibrinogen component in the presence of various critical biological and non-biological agents as envisioned by the instant invention. Marx U.S. Pat. No. 5,651,982 describes the preparation and use of fibrin glue and liposomes wherein said liposomes contain various biological agents. Marx, however, describes only topical application of said sealant. Marx does not envision the novel delivery method of the instant invention which delivers critical agents to discrete sites within the body.

SUMMARY OF THE INVENTION

It is an object of the present invention to provide an improved fibrin sealant which incorporates various critical biological and non-biological agents into the novel sealant. It is a further object of the present invention to present a novel method of reconstituting fibrin sealant in the presence of said agents to provide a sealant with enhanced therapeutic value. It is a further object of the present invention to provide a method of delivering said enhanced sealant to a discrete site within the body in a manner which takes advantage of the bio-static qualities of fibrin sealant to provide superior therapeutic value to the patient by delivering, sealing and holding said agent at critical sites within the body. Optionally, said agent is then slowly released or absorbed at said specific site providing maximum therapeutic value.

DETAILED DESCRIPTION OF THE INVENTION

Figure 1:
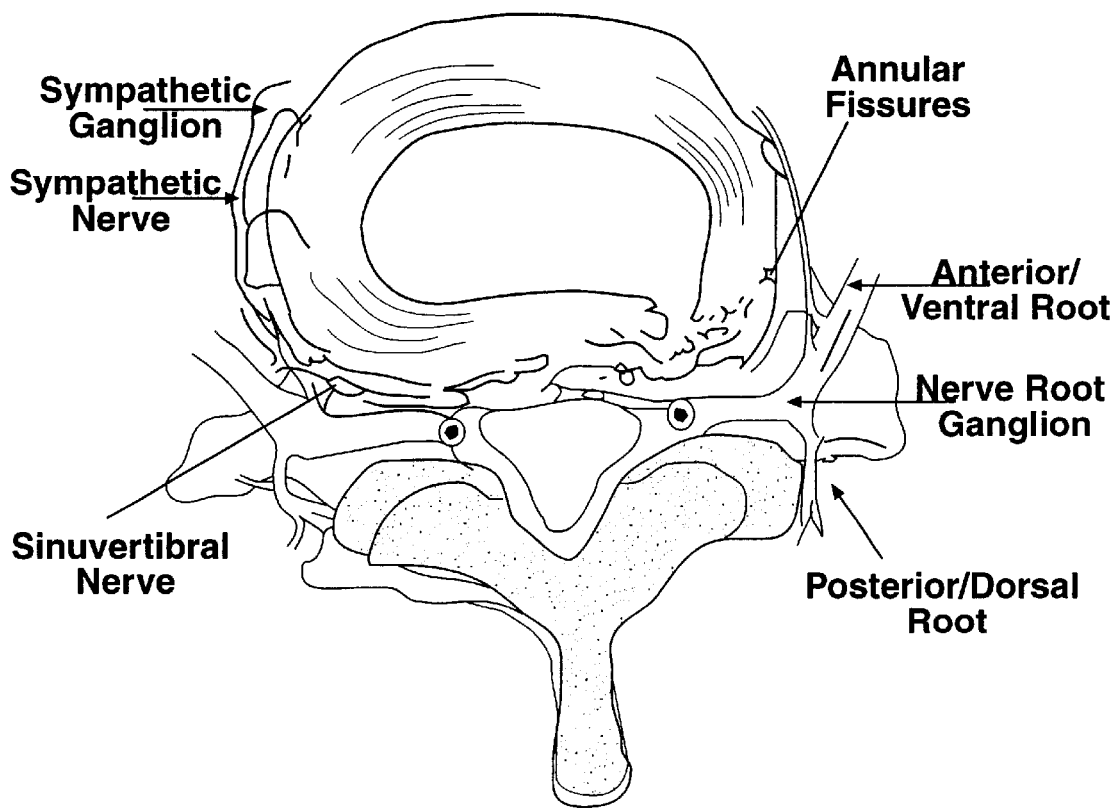
FIG. 1 is a cross sectional view of a vertebral body at the disk space exhibiting annular fissures which are treated according to one embodiment of the present invention.

The present invention describes a novel biological composition which facilitates the precise delivery of various biological and non-biological agents to specific sites within the body. Furthermore, the novel composition utilizes the biological adhesive qualities of fibrin sealant in order to localize and maintain the delivery of the desired agents to the specific site in question. This is accomplished through the tissue adhesive qualities of fibrin sealant. Fibrin sealant mimics the final stage of the natural clotting mechanism. By reconstituting the components of the fibrin sealant in the presence of the desired agent, the agent can then be delivered to the desired site and held in place by the fibrin clot. The agent may then be slowly released or. absorbed over time at the precise location indicated.

The novel product is a combination of the well known two component fibrin sealant along with a biological or non-biological agent. The agent is chosen depending upon the specific application. The known process for fibrin sealant formation entails the mixing of two components, fibrinogen and an activating enzyme such as thrombin. Thrombin is a highly specific protease that transforms the fibrinogen into fibrin. In normal practice, the normally freeze-dried components are reconstituted separately prior to use. Fibrinogen is typically reconstituted in a fibrinolysis inhibitor to prevent premature degradation of the formed fibrin. The reconstituted components are then combined to form the fibrin sealant. Mixing the a fibrinogen and thrombin solutions produces a viscous solution that quickly sets into an elastic coagulum. Preferably, the mixing occurs in a needle mounted on a Y-connector which connects a dual syringe system. In this way, the mixing only occurs in the actual delivery process such that the coagulum forms only at the desired site.

For example, the fibrin sealant may be prepared as described by J. Rousou, et al. in the Journal of Thoracic and Cardiovascular Surgery, vol.97, no.2, pp 194–203, Feb. 1989: Cryoprecipitate derived from source plasma is washed, dissolved in buffer solution, filtered and freeze-dried. The freeze-dried fibrinogen is reconstituted in a fibrinolysis inhibitor solution, for example aprotinin, of 3000 KIU/ml. Aprotinin is a polyvalent protease inhibitor which prevents premature degradation of the formed fibrin.

The solution is stirred and heated to a temperature of about 37° C. The solution must be used within four hours. Freeze-dried thrombin is reconstituted in a calcium chloride solution. The solution is stirred until the thrombin is fully dissolved and kept at a temperature of 37° C. Each solution is drawn up in a syringe and mounted on a Y-connector to which a needle is attached for delivery of the combined solution. (See, e.g. the Duploject®device, from ImmunoAG, Vienna, Austria).

It has been known to use fibrin sealant prepared in the above described manner in a number of clinical applications. Typically, the fibrin sealant is used topically. The novel invention constitutes an improvement over the existing techniques. Said improvement includes a unique preparation protocol and unique delivery systems. The invention envisions reconstituting the thrombin component with various biological and non-biological agents. Said agents are chosen depending upon the indications of the particular patient. Said delivery system provides a novel means for delivering a particular agent to a specific critical site within the body and holding the agent in place thereby optionally providing a prolonged, time-released therapeutic value.

For example, therapeutic spinal injections to treat low back pain and sciatica are well known. The use of corticosteroid injections into the lumbar epidural space for treatment of low back pain and radicular leg pain is well known. It has been found that corticosteroids, such as betamethasone sodium phosphate and betamethasone acetate, ease inflamation of the nerve root. The invention envisions the incorporation of the betamethasone solution into the fibrin sealant. This is done by using the betamethasone solution in place of the calcium chloride solution used to reconstitute the freeze-dried thrombin. The reconstitution of the fibrinogen solution is accomplished in the same manner as described above. All solutions are brought to a temperature of about 37° C. The thrombin/betamethasone solution and the fibrinogen solution are mixed using the dual-syringe procedure described above to form a unique biological sealant composition. The fibrin sealant is now infused with a therapeutic biological agent, namely, betamethasone. The instant invention allows for the delivery of the corticosteroid to the precise area of inflamation in a vehicle which holds the agent in the critical area in a bio-static environment. The novel delivery system delivers the desired agent to a precise, critical site within the body and holds the agent in place, thus providing prolonged, time-released therapeutic value.

Other corticosteroids are envisioned to be used in similar therapies including: triamicinalone and methylprednisolone.

Advantage may be taken of the novel therapeutic qualities of the enhanced fibrin sealant given the sealant's bio-static qualities. For example, fluoroscopic transforaminal lumbar epidural injection of the novel sealant may be of advantage. Use of the novel composition may be better understood by reference to the following examples.

EXAMPLE 1

Fluoroscopic Transforaminal Lumbar Epidural Injection: With the patient in the prone position on the imaging table, the fluoroscope is positioned and adjusted to locate the intervertebral foramen of the affected nerve root. A curved 22ga. ×3.5" needle is introduced after anesthetizing the skin and deep tissue. The needle is advanced under direct fluoroscopic vision to a position in the anterior epidural space. Its position is verified by a lateral fluoroscopic view and further verified by injecting contrast medium through the needle. The needle placement may or may not require further adjustment. If adjusted, location is once again verified. Precise needle placement is also verified by the patient's recognition of the needle stimulating their pain in the same manner of their complaint. The epidural space is anesthetized with injectable anesthetic. The novel fibrin sealant with the accompanying corticosteroid is then introduced through the needle with continuous gentle pressure until the volumes of the dual syringe system are run out. The enhanced fibrin sealant coats the nerve root and annulus. The needle is withdrawn and the patient recovers in the usual manner of observation and vital signs monitoring for a period of 20–30 minutes.

Patients are given routine discharge instructions and asked to call the following day. They also return in seven days or less for evaluation.

Note that a sufficient volume of the enhanced fibrin sealant is injected to effectively hydro-dissect the area around the affected nerve root. The fibrin sealant acts to hold the accompanying corticosteroid in place on the nerve root. It is believed that due to the avascular nature of the epidural space, the absorption/degradation period is extended to a time greater than that observed in open applications in sites with greater vascularity and exposure to room air at the time of application. This is a beneficial phenomenon allowing the corticosteroid to remain at the site of application longer resulting in prolonging its anti-inflammatory effect on the nerve root and surrounding tissue.

A further benefit of the invention is in its ability to seal annular fissures related to disc herniation. Chemical radiculitis is known to contribute to pain factors in patients with back pain. Corticosteroids have been shown to inhibit prostaglandin synthesis and impair the cell-mediated and humoral immune responses. It is believed that use of the novel fibrin sealant in the above described manner not only acts to coat the nerve root, but also acts to seal the annular fissures surrounding the herniated disk. (See FIG. 1). As a result of the hydro-dissection of the area around the affected nerve root, the enhanced sealant also seals the annular fissures from outside the annulus.

Use of fibrin sealant on the dura, as a sealant, has been demonstrated to be effective as described in the study done at the University of Virginia Neurosurgery Department (C. Shaffrey, et al., Neurosurgery. vol.26, No.2, pp 207–210, 1990). The study validates the use of fibrin sealant for its sealing capabilities rather than its hemostatic qualities. Thus, the novel fibrin sealant is multi-functional, acting (1) to seal and protect the exposed nerve root from further chemical damage, and (2) to act as the vehicle to maintain the corticosteroid in a lasting deposition on the nerve root. Furthermore, it is used to seal off the source of the chemical leakage to protect the nerve root from further chemical impairment. The novel enhanced fibrin sealant acts to maintain extended anti-inflammatory response to the corticosteroid and to seal the annular fissures, which otherwise allow damaging chemicals to escape from the disc space and bathe the nerve root resulting in chemical radiculitis.

Patients who have been treated in this manner have had remarkable pain resolution within 24 to 48 hours. It has been noted that further steroid injections have been necessary at other pain generator sites, as they had been masked by the more predominate pain generated at the leaking disc site. Patients often have multiple lesions at various levels.

EXAMPLE 2

Figure 2:
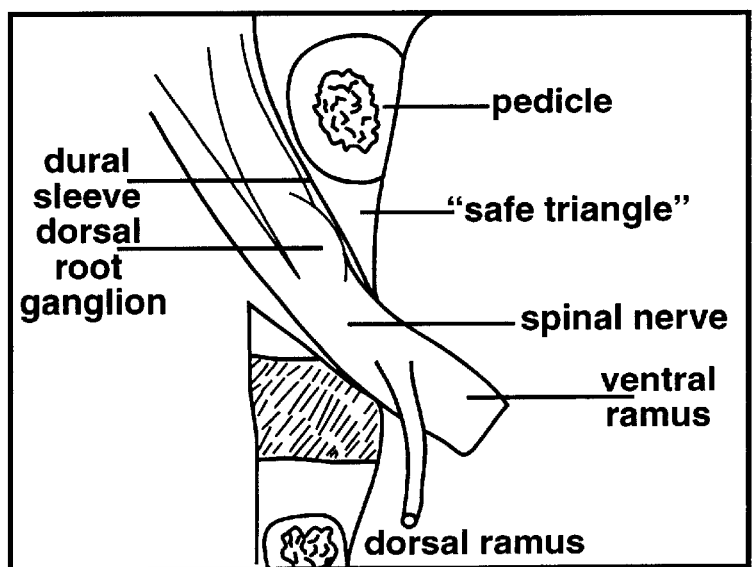
FIG. 2 is a schematic representation of the intra-discal space into which the novel sealant is injected according to one embodiment of the present invention.

Fluoroscopic Transforaminal Lumbar Intra-discal Injection: After the usual sterile preparation, a 20ga. ×3.5" spinal needle is advanced to the corresponding transverse process, then redirected 1 cm anterior and inferior. A curved 25ga. ×6" spinal needle is advanced through the 20ga. introducer needle into the so-called "safe triangle" area. (See G. Lutz, Arch Phys Med Rehabil, vol 79, pp 18–21, November 1998). The "safe triangle" is composed of a roof made up by the pedicle, a tangential base that corresponds to the exiting nerve root, and a side that is made by the lateral border of the vertebral body. (See FIG. 2). Both anterior-posterior and lateral fluoroscopic projections are used to confirm proper needle placement. If the needle placement needs to be adjusted, placement is again confirmed fluoroscopicaly. On the lateral view, the needle should be positioned just below the pedicle in the ventral aspect of the intervertebral foramen. Contrast is injected to confirm needle placement. In patients with chemical radiculitis, the contrast agent can be observed to be leaking through the annular fissures. Once the needle is properly placed in the intra-discal space, the novel enhanced fibrin sealant is injected. The novel sealant is observed to force the contrast agent from the intra-discal space as it seals the annular fissures. The procedure not only soothes the nerve root, and eases inflamation, but also stops the chemical leak and facilitates regeneration within the disc.

The foregoing examples are meant to illustrate certain aspects of carrying out the invention and is not intended to limit the invention in any way.

It is envisioned that the novel invention may be used to address various conditions by use of the novel enhanced fibrin sealant in a manner similar to that described in the examples above. For instance, it is envisioned that harvested cartiledge may be used to grow cells which can be injected in the novel manner at implicated sites such as knee and elbow joints. The novel sealant may be injected under the peri-osteum at the critical site. The enhanced sealant acts to seal the Fats accompanying cells at the critical site. In the same manner, disc cells may be generated and injected intra-discally in the manner described above.

It is also envisioned that the novel invention may be used to aid in facile recovery from radical breast mastectomy. In has been observed that after lymph nodes are removed, lymph fluid continues to leak post-operatively. The novel sealant may be reconstituted with critical chemotherapy agents and used to deliver said agents to the critical site, and then seal the site, thereby preventing further leakage while holding the chemotherapy agent in place.

It is also envisioned that the novel invention may be used to deliver and seal in place suspended antibiotics, gene therapy agents, cell growth agents, analgesics, and replicated cell suspensions at various critical sites within the body.

Discussion of this invention referenced particular means, materials and embodiments elaborating limited application of the claimed invention. The invention is not limited to these particulars and applies to all equivalents.

Although this invention has been described above with reference to particular means, materials and embodiments, it is to be understood that the invention is not limited to these disclosed particulars, but extends instead to all equivalents within the scope of the following claims.

We claim:

1. A biological tissue adhesive comprising combined fibrinogen and thrombin, and a corticosteroid treatment agent, wherein a solution containing the corticosteroid treatment agent is used to reconstitute the thrombin from a freeze-dried state.

2. A biological tissue adhesive as in claim 1, wherein the solution containing the corticosteroid treatment agent is a betamethasone solution.

3. A biological tissue adhesive as in claim 2, wherein the betamethasone solution is a betamethasone sodium phosphate solution.

4. A biological tissue adhesive as in claim 2, wherein the betamethasone solution is a betamethasone acetate solution.

5. A biological tissue adhesive as in claim 1, wherein the solution containing the corticosteroid treatment agent is a triamicinalone solution.

6. A biological tissue adhesive as in claim 1, wherein the solution containing the corticosteroid treatment agent is a methylprednisolone solution.

7. A biological tissue adhesive as in claim 1, made by the method of reconstituting freeze-dried fibrinogin in a fibrinolysis inhibitor solution, reconstituting freeze-dried thrombin in the solution containing the corticosteroid treatment agent, and mixing the reconstituted fibrinogin and reconstituted thrombin in place at a discrete site within a body of a person to form said adhesive containing fibrinogin, thrombin, and corticosteroid treatment agent.

8. A biological tissue adhesive as in claim 7, wherein the solution containing the corticosteroid treatment agent is a betamethasone solution.

9. A biological tissue adhesive as in claim 8, wherein the betamethasone solution is a betamethasone sodium phosphate solution.

10. A biological tissue adhesive as in claims 8, wherein the betamethasone solution is a betamethasone acetate solution.

11. A biological tissue adhesive as in claim 7, wherein the solution containing the corticosteroid treatment agent is a triamicinalone solution.

12. A biological tissue adhesive as in claim 7, wherein the solution containing the corticosteroid treatment agent is a methylprednisolone solution.

13. A method of making a biological tissue adhesive, the method comprising reconstituting freeze-dried fibrinogin in a fibrinolysis inhibitor solution, reconstituting freeze-dried thrombin in a solution containing a corticosteroid treatment agent, and mixing the reconstituted fibrinogin and reconstituted thrombin in the corticosteroid treatment agent solution at a site in a person's body to form an adhesive in the body containing fibrinogin, thrombin, and corticosteroid treatment agent.

14. A method as in claim 13, wherein said mixing comprises placing the reconstituted, fibrinogin in a first syringe of a dual syringe system and placing the reconstituted thrombin in the corticosteroid treatment agent solution in a second syringe of the dual syringe system, and performing said mixing by forcing the reconstituted fibrinogin and the reconstituted thrombin in the corticosteroid; treatment agent into a needle mounted on a Y-connector of said dual syringe system that connects said first syringe and said second syringe, and wherein said needle is at the site within the person's body.

* * * * *